(12) United States Patent
Inchley et al.

(10) Patent No.: US 7,780,977 B2
(45) Date of Patent: Aug. 24, 2010

(54) MEDICATION COMPOSITIONS

(75) Inventors: Andrew John Inchley, Nottingham (GB); Kenneth Donald Vaughan, Nottingham (GB)

(73) Assignee: Bioprogress Technology Limited, Cambridgeshire (GB)

( * ) Notice: Subject to any disclaimer, the term of this patent is extended or adjusted under 35 U.S.C. 154(b) by 1684 days.

(21) Appl. No.: 10/481,056

(22) PCT Filed: Jun. 11, 2002

(86) PCT No.: PCT/GB02/02637

§ 371 (c)(1),
(2), (4) Date: Sep. 27, 2004

(87) PCT Pub. No.: WO02/102356

PCT Pub. Date: Dec. 27, 2002

(65) Prior Publication Data

US 2005/0042276 A1    Feb. 24, 2005

(30) Foreign Application Priority Data

Jun. 16, 2001   (GB)   ................... 0114746.1

(51) Int. Cl.
*A61K 9/48* (2006.01)
*A61K 47/06* (2006.01)
*A23L 1/03* (2006.01)

(52) U.S. Cl. ...................................... 424/439; 514/343
(58) Field of Classification Search ................ 424/439; 514/343

See application file for complete search history.

(56) References Cited

U.S. PATENT DOCUMENTS

| 4,425,332 | A | * | 1/1984 | James | ...................... 424/94.3 |
| 4,684,534 | A | | 8/1987 | Valentine | |
| 4,931,285 | A | * | 6/1990 | Edgren et al. | ................ 424/473 |

FOREIGN PATENT DOCUMENTS

| CN | 1203792 | 1/1999 |
| DE | 199 22537 | 11/2000 |
| JP | EP 1163901 | 12/2001 |
| NL | EP 0491443 | 6/1992 |
| WO | WO 98/02140 | 1/1998 |

\* cited by examiner

*Primary Examiner*—Ardin Marschel
*Assistant Examiner*—Zohreh Vakili
(74) *Attorney, Agent, or Firm*—McDermott Will & Emery LLP

(57) ABSTRACT

A medicinal composition comprising: (a) a core comprising a medicinally effective unit dose of one or more active medicaments; and (b) said medicament(s) being enclosed within a film material which comprises at least 40% by weight hydroxypropylmethyl cellulose.

12 Claims, No Drawings

MEDICATION COMPOSITIONS

TECHNICAL FIELD

The present invention relates to medicinal compositions which are easier to administer to patients such as children, the aged or the infirm who have difficulty swallowing solid dosage forms such as tablets and capsules.

BACKGROUND ART

Many members of the population have difficulty in swallowing solid dosage forms. This is particularly true for the very young, the old and the infirm but can also apply to others particularly if there is not a ready supply of liquid (eg water) to wash down the solid dosage forms.

If the active medicament to be administered has a taste which is perceived by the patient to be unpleasant, then the patient will be less inclined to take the medicament. Several methods of overcoming or masking the taste of unpleasant tasting medicaments have been proposed. Many of these involve coating either the solid dosage form or smaller particles containing the medicament with a material which does not dissolve or disperse in the mouth. Coatings of this type can however slow down the absorption of the active medicament as the coating must be removed before the active medicament can be absorbed either in the stomach or in the gastrointestinal tract.

Another solution to the problem of administering medicines to those who find it difficult to swallow solid dosage forms is to use liquid or gel compositions containing the active medicament. These compositions are not however suitable for everyone. The amount of liquid or gel formulation can vary from dose to dose as the patient or a carer has to dispense an appropriate amount of the composition for example by pouring the composition into a measuring spoon or container. If insufficient care is taken doing this the patient may not be given the intended dose of the active medicament. There is also the possibility that some or all of the intended dose will be spilled before it can be administered, particularly if the patient is reluctant or not in a reasonable physical condition to take the medicine or is uncooperative.

SUMMARY OF THE INVENTION

The present invention provides a medicinal composition which avoids the problems described above with known solid, liquid and gel dosage forms but does enable the patient to be given an accurate dose of the active medicament.

The present invention provides a medicinal composition which comprises
 a) a core comprising a medicinally effective unit dose of one or more active medicaments; and
 b) said medicaments being enclosed within a film material which comprises at least 40% by weight hydroxypropylmethyl cellulose.

The film material is preferably composed of 40-100% by weight hydroxypropylmethyl cellulose (HPMC), more preferably 40-80% by weight of the film HPMC with 20-60% of one or more plasticisers. Suitable plasticisers include polyethyleneglycols, diacetin, propyleneglycols or glycerin. Other components such as colouring agents, flavours, fruit acids and/or sweeteners may be added to the film material. The film material may be expanded for example by pumping gas (eg nitrogen gas) into a concentrated solution of the polymer and drying the resulting mixture. However, a non-foamed (i.e. non-expanded) film material is preferred.

DETAILED DESCRIPTION OF THE INVENTION

In a preferred embodiment, the core is a fondant core, and the core and the encapsulating film preferably provide a synergistic effect in that the encapsulating film contains and protects the core and the core supports the film. In this way, a relatively thin film may be used to encapsulate the core, which has the advantage of dissolving rapidly in the mouth.

By the term "fondant core", it is meant a fine crystalline sugar dispersed within a low melting point solid organic carrier.

The solid organic carrier preferably has a melting point in the range 22 to 60° C., preferably 25 to 40° C., more preferably 32 to 34° C. Examples of suitable solid organic carriers include hydrogenated coconut oil; Polyethylene glycol, for example selected from the PEG 1000, PEG 2000 and PEG 3000 ranges of polyethylene glycols; povidone; and gelucire.

The sugar component of the fondant core preferably has a weight average particle size in the range 1-150 µm, more preferably 10-100 µm and most preferably 10-25 µm. The sugar is preferably selected from sucrose, fructose, glucose, trehalose and lactose, although any suitable sugar could be used. Sugar derivatives may also be used either in addition to the sugar or as an alternative to it, provided that the sugar or sugar derivative has the required particle size properties and is pharmaceutically acceptable.

The fondant core preferably has certain physical characteristics which enable it to provide the HPMC film with a desired degree of support. In particular, the fondant core preferably has a viscosity of at least 10 Pa.s at a sheer stress of 1 Pa measured at 36° C. Desirably, the fondant core viscosity is at least 50 Pa.s, more preferably at least 100 Pa.s. and most preferably at least 1000 Pa.s when measured at 36° C. at a sheer stress of 1.0 Pa. The viscosity may be measured using an AR 2000 Rheometer with a 20 mm cross-hatched steel plate.

In addition, the fondant core should preferably exhibit a peak normal force of at least 0.1N, more preferably at least 1N, most preferably at least 5N during a squeeze flow test conducted at 36° C. over 500 seconds at a compression rate of 10 µm/sec using a sample disc 4-8 mm in diameter and up to 500 µm thick. The squeeze flow test measures the biaxial extension (squeeze and subsequent rate of movement) of the sample when compressed. The test may be carried out using an AR 2000 Rheometer fitted with 8 mm steel plates.

The preferred fondant core dissolves or disperses rapidly in the mouth of a consumer. This preferably occurs within 10 to 90 seconds after exposure of the core to saliva, preferably 20 to 80 seconds, more preferably 30 to 60 seconds. However, in certain circumstances, e.g. where the capsule is intended to treat a sore throat, it may be desired to have a longer dissolution/dispersion time, e.g. up to 300 seconds, to provide a soothing sensation over a longer period of time.

The preferred fondant core has the advantage of being a solid or semi-solid when encapsulated within the HPMC-containing film at 20-25° C. (i.e. room temperature). This provides the film with the desired degree of support and results in a robust medicinal product. However, once exposed to saliva, the core dissolves and/or disperses to provide the consumer with a desirable "melt in the mouth" feeling. This assists in soothing for example sore throats and irritating coughs, without the formulation and production problems associated with providing a liquid-containing medicament.

Thus, the benefits of a liquid-containing medicament may be obtained without having to use, for example, a relatively thick and slow dissolving encapsulating film in order to provide the end product with sufficient robustness and strength for it to be commercially acceptable.

The active medicament may be an analgesic or anti-inflammatory, decongestant, cough suppressant, expectorant, mucolytic, antihistamine, antiallergy agent, agent for treating the gastrointestinal tract (for example antacid, antireflux agent, antiulcer agent, antidiarrhoeal agent, laxative or antiemetic), agent to counter motion sickness, antiviral agents, antifungal agents, antibacterial agents, diuretic agents, antiasthmatic agents, antimigraine agents, antianxiety agents, tranquilising agents, sleep promoting agents, vitamins and/or minerals, natural products and extracts thereof (for example herbs or naturally occurring oils)

Suitable analgesics include aspirin, paracetamol (acetaminophen) and non-steroidal anti-inflammatory/analgesics such as diclofenac, indomethacin, mefanamic acid, nabumetone, tolmetin, piroxicam, felbinac, diflunisal, ibuprofen, flurbiprofen, naproxen and ketoprofen, active isomers thereof or medicinally acceptable salts thereof (for example the sodium or lysine salts) or narcotic analgesics such as codeine and medicinally acceptable salts thereof (for example codeine phosphate or sulphate). Caffeine may be present in analgesic products to enhance the analgesic effect.

The amount of aspirin in a unit dose may be in the range 75 to 800 mg, preferably 200-600 mg, most preferably 75, 150, 300, 400 or 600 mg. The amount of paracetamol in a unit dose may be 50 to 2000 mg, preferably 120 to 1000 mg, most preferably 120, 250, 500 or 1000 mg. The amount of diclofenac in a unit dose may be 10 to 100 mg, preferably 20 to 80 mg, most preferably 25 or 50 mg. The amount of indomethacin in a unit dose may be in the range 25-75 mg, preferably 25 mg, 50 mg or 75 mg. The amount of mefanamic acid in a unit dose may be in the range 250-500 mg, preferably 250 mg or 500 mg. The amount of nabutmetone in a unit dose may be in the range 500-1000 mg. The amount of piroxicam in a unit dose may be in the range 10-40 mg, preferably 10, 20 or 40 mg. The amount of diflunisal in a unit dose may be in the range 250-500 mg, preferably 250 mg or 500 mg. The amount of ibuprofen in a unit dose may be in the range 50 to 800 mg, preferably 100 to 400 mg, most preferably 100, 200 or 400 mg. The amount of flurbiprofen in a unit dose may be 5 to 200 mg, preferably 5 to 150 mg, most preferably 50 or 100 mg. The amount of naproxen in a unit dose may be 100 to 800 mg, preferably 200 to 600 mg, most preferably 250, 373 or 500 mg. The amount of ketoprofen in a unit dose may be 25 to 250 mg, preferably 50 to 150 mg, most preferably 50 or 100 mg. The amount of codeine in a unit dose may be 20 to 50 mg, preferably 5 to 30 mg, most preferably 8, 12.5, 16 or 25 mg. If medicinally effective salts of the above compounds are used then the amount of salt should be increased to give a dose of the free medicament corresponding to the figures given above. The amount of caffeine in a unit dose may be 5 to 200 mg, preferably 10 to 100 mg, most preferably 30, 45, 60 or 100 mg.

Suitable decongestants include ephedrine, levomethol, pseudoephedrine preferably as its hydrochloride, phenylpropanolamine preferably as its hydrochloride and phenylephrine.

The amount of ephedrine in a unit dose may be in the range 15-60 mg. The amount of levomethol in a unit dose may be in the range 0.5-100 mg, preferably 0.5-25 mg, most preferably 1, 2, 5, 10 or 25 mg. The amount of pseudoephedrine preferably as its hydrochloride in a unit dose may be in the range 60-120 mg, preferably 30, 60 or 120 mg. The amount of phenylpropanolamine preferably as its hydrochloride in a unit dose may be in the range 5-50 mg, preferably 5-20 mg. The amount of phenylephrine in a unit dose may be in the range 5-25 mg, preferably 5, 10 or 25 mg.

Suitable cough suppressants include bibenzonium preferably as its bromide, caramiphen, carbetapentane preferably as its citrate, codeine, dextromethorphan preferably as its hydrobromide or an absorbate thereof, noscapine and pholcodine.

The amount of bibenzonium bromide in a unit dose may be in the range 20-30 mg. The amount of caramiphen in a unit dose may be in the range 5-20 mg, preferably 5 or 20 mg. The amount of carbetapentane citrate in a unit dose may be in the range 15-30 mg. The amount of codeine in a unit dose maybe in the range 2-50 mg, preferably 5-30 mg, most preferably 10 mg. In the present invention medicinally acceptable salts of codeine may also be used (for example codeine phosphate or sulphate). The amount of dextromethorphan hydrobromide in a unit dose may be in the range 5-60 mg, preferably 15 or 30 mg. The amount of noscapine in a unit dose may be in the range 15-30 mg. The amount of pholcodeine in a unit dose may be in the range 2-25 mg, preferably 5 to 20 mg, more preferably 10 to 15 mg.

Suitable expectorants include ammonium bicarbonate, ammonium chloride, bromhexine hydrochloride, cocillana creosote, guaifenesin, ipecacuanha, potassium and medicinally acceptable salts thereof (for example potassium citrate or iodide), potassium guaicolsulfonate, squill and terpin hydrate.

The amount of ammonium bicarbonate in a unit dose may be in the range 300-600 mg. The amount of ammonium chloridein in a unit dose may be in the range 0.3-2 g (300-2000 mg). The amount of bromhexine hydrochloride in a unit dose may be in the range 24-64 mg. The amount of cocillana creosote in a unit dose may be in the range 0.12-0.6 ml. The amount of guaifenesin in a unit dose may be in the range 100-200 mg, preferably 100 mg. The amount of ipecacuanha in a unit dose may be in the range 25-100 mg. The amount of potassium iodide in a unit dose may be in the range 150-300 mg, preferably 100 mg. The amount of potassium citrate in a unit dose may be in the range 150-300 mg, preferably 100 mg. The amount of potassium guaicolsulfonate in a unit dose may be 80 mg. The amount of squill in a unit dose may be in the range 60-200 mg. The amount of terpin hydrate in a unit dose may be in the range 125-600 mg, preferably 300 mg.

Suitable mucolytic agents include ambroxyl, acetylcystine and carbocisteine

The amount of carbocisteine in a unit dose may be in the range 100 mg to 1000 mg, preferably 200 to 500 mg Suitable antihistamines include azatadine or a salt thereof such as the maleate, bromodiphenhydramine or a salt thereof such as the hydrochloride, brompheniramine or a salt thereof such as the maleate, carbinoxamine or a salt thereof such as the maleate, chlorpheniramine or a salt thereof such as the maleate, cyproheptadine or a salt thereof such as the hydrochloride, dexbrompheniramine or a salt thereof such as the maleate, dexchlorpheniramine or a salt thereof such as the maleate, diphenhydramine or a salt thereof such as the hydrochloride, doxylamine or a salt thereof such as the succinate, phenidamine or a salt thereof such as the tartrate, promethazine or a salt thereof such as the hydrochloride, pyrilamine or a salt thereof such as the maleate, pyrilamine or a salt thereof such as the tannate, tripelennamine or a salt thereof such as the hydrochloride, tripolidine or a salt thereof such as the hydrochloride, cetirizine or a salt thereof such as the hydrochloride, cinnarizine, mequitazine, acrivastine.

The amount of azatadine in the form of maleate in a unit dose may be in the range 1-2 mg, preferably 1 mg. The amount of bromodiphenhydramine in the form of hydrochloride in a unit dose may be 3.75 mg. The amount of brompheniramine in the form of maleate in a unit dose may be in the range 4-12 mg, preferably 4, 8 or 12 mg. The amount of carbinoxamine in the form of maleate in a unit dose may be 4 mg. The amount of chlorpheniramine in the form of maleate in a unit dose may be in the range 2-12 mg, preferably 4, 8 or 12 mg. The amount of dexbrompheniramine in the form of maleate in a unit dose may be 6 mg. The amount of dexchlorpheniramine in the form of maleate in a unit dose may be in the range of 2-6 mg, preferably 2, 4 or 6 mg. The amount of diphenhydramine in the form of hydrochloride in a unit dose may be in the range of 12.5 to 200 mg, preferably 12.5-50 mg, more preferably 12.5, 25 or 50 mg. The amount of doxylamine in the form of succinate in a unit dose may be in the range 7.5-10 mg, preferably 7.5 or 10 mg. The amount of phenidamine in the form of tartrate in a unit dose may be in the range 5-10 mg, preferably 5 or 10 mg. The amount of promethazine in the form of hydrochloride in a unit dose may be in the range 1.5-6 mg. The amount of pyrilamine in the form of maleate in a unit dose may be 12.5 mg. The amount of pyrilamine in the form of tannate in a unit dose may be 12.5 mg. The amount of tripelennamine in the form of hydrochloride in a unit dose may be in the range 25-50 mg, preferably 25, 37.5 or 50 mg. The amount of triprolidine in the form of hydrochloride in a unit dose may be in the range 1-2.5 mg, preferably 1.25-2.5 mg, most preferably 1.25 mg. The amount of cetirizine in a unit dose may be in the range 5-10 mg, preferably 5 mg or 10 mg. The amount of cinnarizine in a unit dose may be in the range of 15-75 mg, preferably 15 mg or 75 mg. The amount of mequitazine in a unit dose may be in the range 5-10 mg, preferably 5 mg or 10 mg. The amount of acrivastine in a unit dose may be 3-20 mg, preferably 5-10 mg, most preferably around 8 mg.

Suitable antiallergy agents include astemizole, clemastine or a salt thereof such as the hydrogen fumerate, loratadine, terfenadine.

The amount of astemizole in a unit dose may be in the range 0.5-200 mg, preferably 1-100 mg, most preferably 2, 5, 10, 20 or 40 mg. The amount of clemastine in the form of its hydrogen fumerate in a unit dose may be in the range 0.01-200 mg, preferably 0.1-10 mg, most preferably 0.2, 0.4, 0.6, 1.2 or 2.4 mg. The amount of loratadine in a unit dose may be in the range 0.5-200 mg, preferably 1-100 mg, most preferably 2, 5, 10, 20 or 40 mg. The amount of terfenadine in a unit dose may be in the range 5-1000 mg, preferably 10-600 mg, most preferably 20, 40, 60, 100 or 200 mg.

Suitable antacids include aluminium glycinate, aluminium hydroxide gel, aluminium phosphate gel, dried aluminium phosphate gel, calcium carbonate, charcoal, hydrotalcite, light kaolin, magnesium carbonate, magnesium hydroxide, magnesium oxide, magnesium trisilicate, sodium bicarbonate.

The amount of aluminium glycinate in a unit dose may be in the range 0.1-10 g, preferably 0.1-5 g, most preferably 0.2, 0.5, 1 or 2 g. The amount of aluminium hydroxide gel in a unit dose may be in the range 1-50 ml, preferably 2-30 ml, most preferably 5, 7.5, 10, 15 or 30 ml. The amount of aluminium phosphate gel in a unit dose may be in the range 0.5-100 ml, preferably 1-50 ml, most preferably 2, 5, 10, 15 or 30 ml. The amount of dried aluminium phosphate gel in a unit dose may be in the range 50-5000 mg, preferably 100-2000 mg, most preferably 200, 400, 800 or 1600 mg. The amount of calcium carbonate in a unit dose may be in the range 0.1-30 g, preferably 0.5-10 g, most preferably 0.5, 1, 2 or 5 g. The amount of charcoal in a unit dose may be in the range 1-200 g, preferably 1-100 g, most preferably 2, 4, 8, 16 or 50 g. The amount of hydrotalcite in a unit dose may be in the range 0.1-10 g, preferably 0.2-5 g, most preferably 0.5, 1 or 2 g. The amount of light kaolin in a unit dose may be in the range 10 mg-100 g, preferably 100 mg-75 g, most preferably 1, 10, 15, 20, 50 or 75 g. The amount of magnesium carbonate in a unit dose may be in the range 50 mg-10 g, preferably 50 mg-5 g, most preferably 100, 200 or 500 mg. The amount of magnesium hydroxide in a unit dose may be in the range 100 mg-10 g, preferably 100 mg-5 g, most preferably 100, 250, 500 or 750 mg. The amount of magnesium oxide in a unit dose may be in the range 100 mg-10 g, preferably 100 mg-5 g, most preferably 100, 250, 500 or 750 mg. The amount of sodium bicarbonate in a unit dose may be in the range 0.1-50 g, preferably 0.5-25 g, most preferably 0.5, 1, 2, 5 or 10 g.

Suitable antireflux agents include simethicone and sodium alginate.

The amount of simethicone in a unit dose may be in the range 5-1000 mg, preferably 10-500 mg, most preferably 25, 40, 50, 60, 100 or 200 mg. The amount of sodium alginate in a unit dose may be in the range 50 mg-10 g, preferably 75 mg-5 g, most preferably 100, 250, 500 or 1 g.

Suitable antiulcer agents include bismuth subsalicylate, $H_2$ receptor antagonists such as cimetidine, famotidine, ranitidine and nizatidine and proton pump inhibitors such as omeprazole, pantoprazole and lansoprazole.

The amount of bismuth subsalicylate in a unit dose may be in the range 250-2000 mg, preferably 50-1500 mg, most preferably 75, 150, 300, 600 or 1000 mg. The amount of cimetidine in a unit dose may be in the range 10 mg-5 g, preferably 50 mg-2 g, most preferably 100, 200 or 400 mg. The amount of famotidine in a unit dose may be in the range 10-80 mg, preferably 20 or 40 mg. The amount of ranitidine in a unit dose may be in the range 100-600 mg, preferably 300-600 mg, most preferably 300 or 600 mg. The amount of nizatidine in a unit dose may be 50 to 500 mg, preferably 100 to 400 mg, more preferably 150 to 300 mg. The amount of omeprazole in a unit dose may be 5 to 50 mg, preferably 10 to 40 mg, more preferably 10, 20 or 40 mg. The amount of pantoprazole in a unit dose may be 10 to 50 mg, preferably 15 to 45 mg, more preferably 20 to 40 mg. The amount of lansoprazole in a unit dose may be 5 to 50 mg, preferably 10 to 40 mg, more preferably 15 or 30 mg.

Suitable antidiarrhoeal agents include loperamide or a salt thereof, such as the hydrochloride, methylcellulose, diphenoxylate and morphine or a salt thereof, such as the hydrochloride.

The amount of loperamide in the form of its hydrochloride in a unit dose may be in the range 0.1-50 mg, preferably 0.5-20 mg, most preferably 1, 2, 4 or 8 mg. The amount of methylcellulose in a unit dose may be in the range 20 mg-5 g, preferably 50 mg-4 g, most preferably 100, 200, 500 mg, 1 or 2 g. The amount of diphenoxylate in the form of its hydrochloride in a unit dose may be 1-10 mg, preferably 2-5 mg, more preferably 2.5 mg. The amount of morphine in the form of its hydrochloride in a unit dose may be in the range 20-4000 µg, preferably 50-2000 µg, most preferably 100, 200, 400, 800 or 1600 µg.

Suitable laxatives include agar, aloin, bisacodyl, ispaghula husk, lactulose, phenolphthalein and senna extract (including sennosides A+B).

The amount of agar in a unit dose may be in the range 1-200 mg, preferably 2-100 mg, most preferably 2.5, 5, 10, 20 or 50 mg. The amount of aloin in a unit dose may be in the range 1-200 mg, preferably 2-100 mg, most preferably 5, 10, 15 or 30 mg. The amount of bisacodyl in a unit dose may be in the range 0.1-100 mg, preferably 0.5-50 mg, most preferably 1, 2, 5, 10 or 20 mg. The amount of ispaghula husk in a unit dose may be in the range 100 mg-50 g, preferably 500 mg-25 g, most preferably 1, 2, 3, 5 or 10 g. The amount of lactulose in a unit dose may be in the range 100 mg-50 g, preferably 500 mg-30 g, most preferably 1, 2, 5, 10 or 15 g. The amount of phenolphthalein in a unit dose may be in the range 1-5000 mg, preferably 5-4000 mg, most preferably 7.5, 15, 30, 60, 100, 200 or 300 mg. The amount of senna extract (including sennosides A+B) in a unit dose may be in the range 0.5-100 mg, preferably 1-50 mg, most preferably 2.5, 5, 7.5, 10, 15 or 30 mg.

Suitable antiemetics include dimenhydrinate, metoclopromide or a salt thereof such as the hydrochloride, domperidone or a salt thereof such as the maleate, buclizine, cyclizine, prochlorperazine or a salt thereof such as the maleate, ipecacuanha, squill.

The amount of ipecacuanha in a unit dose may be in the range 25-100 mg. The amount of squill in a unit dose may be in the range 60-200 mg. The amount of domperidone may be in the range 5-50 mg, preferably 5, 10, 15, 20, 25, 30, 40 or 50 mg. The amount of buclizine in a unit dose may be in the range 2-100 mg, preferably 5-50 mg, more preferably 6.25, 13.5, 25. The amount of cyclizine in a unit dose may be in the range 1-50 mg, preferably 2-30 mg, more preferably 5, 7.5, 10, 15, 20 or 25 mg. The amount of metoclopromide in a unit dose may be in the range 2-30 mg, preferably 5, 10, 15 or 30 mg. The amount of dimenhydrinate in a unit dose may be in the range 5-50 mg, preferably 25 mg. The amount of prochlorperazine in a unit dose may be in the range 3-25 mg, preferably 3 mg or 5 mg. If medicinally effective salts of the above compounds are used then the amount of salt should be increased to give a dose of the free medicament corresponding to the figures given above.

Suitable agents to counter motion sickness include cinnarizine, dimenhydrinate, hyoscine or a salt thereof such as the hydrobromide and meclozine or a salt thereof such as the hydrochloride.

The amount of cinnarizine in a unit dose may be in the range 0.5-200 mg, preferably 1-100 mg, most preferably 5, 10, 20, 40 or 60 mg. The amount of dimenhydrinate in a unit dose may be in the range 1-500 mg, preferably 5-300 mg, most preferably 10, 20, 50, 100 or 250 mg. The amount of hyoscine hydrobromide in a unit dose may be in the range 0.01-1 mg, preferably 0.05-0.5 mg, most preferably 0.05, 0.1, 0.2, 0.3 or 0.5 mg. The amount of meclozine hydrochloride in a unit dose may be in the range 0.5-200 mg, preferably 1-100 mg, more preferably 2, 5, 10, 20 or 40 mg.

Suitable antiviral agents include aciclovir. The amount of aciclovir in a unit dose may be in the range 100 to 1000 mg, preferably 200 to 800 mg.

Suitable antifungal agents include fluconazole and terbinafine. The amount of fluconazole in a unit dose may be in the range 50-200 mg, preferably 50 mg or 200 mg. The amount of terbinafine may be in the range 250-500 mg, preferably 250 mg.

Suitable antibacterial agents include erythromycin and fusidic acid and salts thereof such as the sodium salt. The amount of erythromycin in a unit dose may be in the range 125-500 mg, preferably 125 mg, 250 mg or 500 mg. The amount of fusidic acid in a unit dose may be in the range 250-500 mg, preferably 250 mg.

Suitable diuretics include frusemide. The amount of frusemide in a unit dose may be in the range 20-80 mg, preferably 20, 40 or 80 mg.

Suitable anti-asthmatic agents include ketotifen. The amount of ketotifen in a unit dose may be in the range 1-4 mg, preferably 1 mg or 2 mg.

Suitable anti-migraine agents include the triptans such as sumatriptan. The amount of sumatriptan in a unit dose may be in the range 20-100 mg, preferably 20, 50 or 100 mg.

Suitable vitamins include A, B1, B2, B3, B5, B6, B12, C, D, E, folic acid, biotin, and K. Suitable minerals include calcium, phosphorus, iron, magnesium, zinc, iodine, copper, chloride, chromium, manganese, molybdenum, nickel, potassium, selenium, boron, tin and vanadium.

The term active medicament as used herein also embraces materials which are known and used to give relief or comfort to a patient even if they have not been shown to have any pharmacological effect. These are referred to hereinafter as "relief agents". Examples of such materials include anise oil, treacle, honey, liquorice and menthol.

Preferred actives are analgesics, antacids, decongestants, cough suppressants, expectorants, mucolytic agents and laxatives. In addition, relief agents may preferably be incorporated in the composition, either alone or in combination with other actives.

The active is preferably a solid component.

The active medicament(s) may be taste masked to further improve the taste profile of the medicinal composition. The medicament(s) may be taste masked using methods known in the art, for example adding to the core taste masking ingredients such as ethylcellulose, hydroxypropylmethylcellulose, methylethylcellulose, hydroxypropylcellulose, polyvinyl pyrrolidone, polyvinyl alcohol, mono glycerides, diglycerides, stearic acid, palmitic acid, gelatin, hydrogenated cotton seed oil and more generally any food grade polymer, starch, wax or fat. The taste masking agents may be used singly or in combination. The amount of the taste masking ingredient may be in the range by weight of the medicament(s) used.

The core may optionally include other excipients. The other excipients may include taste masking agents, artificial sweeteners, flavours, inert diluents, binders, lubricants.

Suitable taste masking agents are listed above.

Suitable artificial sweeteners include acesulfame K, sodium saccharin, aspartame. The amount of sweetener may be in the range 0.001% to 2%.

Suitable flavours are commercially available and may be enhanced by the addition of an acid, for example citric acid, ascorbic acid, tartaric acid.

Suitable inert diluents include calcium phosphate (anhydrous and dihydrate), calcium sulphate, carboxymethylcellulose calcium, cellulose acetate, dexrates, dextrin, dextrose, fructose, glyceryl palmitostearate, hydrogenated vegetable oil, kaolin, lactitol, lactose, magnesium carbonate, magnesium oxide, maltitol, maltodextrin, maltose, microcrystalline cellulose, polymethacrylates, powdered cellulose, pregelatinised starch, silicified microcrystalline cellulose, sodium chloride, starch, sucrose, sugar, talc, xylitol. One or more diluents may be used. The amount of diluent may be in the range 10-98% w/w.

Suitable binders include acacia, alginic acid, carboxymethylcellulose, cellulose, dextrin, ethylcellulose, gelatin, glucose, guar gum, hydrogenated vegetable oil, hydroxyethylcellulose, hydroxypropylmethylcellulose, liquid glucose, magnesium aluminium silicate, maltodextrin, methylcellulose, polyethylene oxide, polymethacrylates, povidone, sodium alginate, starch, vegetable oil and zein. One or more binders may be used. The amount of binder may be in the range 10-95% w/w.

Suitable lubricants include calcium stearate, canola oil, glyceryl palmitostearate, hydrogenated vegetable oil, magnesium stearate, mineral oil, poloxamer, polyethylene glycol, polyvinyl alcohol, sodium benzoate, sodium lauryl sulphate, sodium stearyl fumarate, stearic acid, talc and zinc stearate.

One or more lubricants may be used. The lubricant may be in the range 0.01-10% w/w.

The core preferable contains substantially no free or unbound water. This is because the film material of the capsule shell is cold water soluble. However, bound water, e.g. present as part of a carbohydrate solution such as a syrup, is acceptable, up to levels of about 40% by weight of the core. By "substantially no free or unbound water", it is meant that the core preferably contains less than 1% by weight free or unbound water, more preferably less than 0.1% by weight, even more preferably less than 0.05% by weight and most preferably 0% by weight free or unbound water.

The film material which is used to encapsulate the core contains hydroxypropylmethyl cellulose (HPMC), preferably in the form of a non-foamed film. The film typically includes a plasticiser to give the film desired properties, such as flexibility. Examples of materials which may be used as plasticisers in the film include polyethylene glycol (PEG), monopropylene glycol, glycerol and acetates of glycerol (acetins).

The film typically has a thickness in the range 20-300 μm, preferably 30-200 μm, more preferably 40-150 μm, most preferably 50-100 μm. It is desired to use as thin a film as possible in order to provide relatively short dissolution times of the composition in the mouth. It will be appreciated that the thicker the film, the longer the dissolution time will be.

Compositions in accordance with the present invention are intended to deliver the active medicament(s) carried in the core to the oral cavity or throat of the user. This is particularly useful if the active medicament is intended to treat coughs, sore throats, toothache, or ease respiratory blockages.

In use, the film starts to dissolve almost immediately after introduction into the mouth. The dissolution may be aided by the action of sucking or chewing performed by the user. The film material dissolves completely in the mouth after a short time and leaves no unpleasant residues. The dissolution time is dependent upon the film thickness, but is usually less than one minute, typically less than 30 seconds and possibly even quicker, e.g. only a few seconds.

Thus, the compositions of the present invention are intended to be ruptured in the mouth of the user for release of the core into the mouth. In other words, the compositions of the present invention comprise an edible delivery vehicle.

The film may include optional components, such as colourants, flavourings, texture modifiers and/or acid materials. The acid materials, such as organic acids, e.g. citric acid, provide an improved mouth feel for the consumer.

The encapsulating film may include an outer coating conventionally used in oral medicaments.

To produce the film, HPMC, typically in the form of a powder is mixed with the plasticiser (if present) and water to produce an aqueous solution. The further components (if present) are then dissolved or dispersed in the solution. A layer of the solution is then cast onto a suitable substrate, e.g. a conveyor belt, and the water removed, e.g. by heating with hot air, to form a dried film which is removed from the substrate.

The film is then used to encapsulate a core as described above. The encapsulation process may use any conventional process, e.g. as disclosed in WO97/355537, WO00/27367 or WO01/03676.

Although the film material is cold water soluble, the resulting capsules are nevertheless found to be sufficiently robust to withstand the production and packaging processes. In addition, they may be held in the hand without the film wall dissolving or rupturing prematurely. However, it will be appreciated that prolonged contact with sweat or other skin secretions may lead to the eventual dissolution of the film wall.

The medicinal formulations according to the present invention may be prepared by forming a first sheet of hydroxypropylmethyl cellulose with a plurality of depressions (for example by vacuum forming techniques), placing the material which comprises the core into the depressions, sealing a planar second sheet of hydroxypropylmethyl cellulose on top of the first sheet to enclose the core material, for example by adhesive or heat sealing, and cutting the individual dosage forms from the sheet.

Alternatively, the medicinal compositions of the present invention may be prepared by placing the core between two sheets of the film material and sealing the sheets together around the periphery of the core. The sheets may be sealed by using an adhesive, a solvent for the material comprising the sheets, by heat or radio frequency welding. Where the core is molten, a pocket may be formed between the two sheets of material into which the molten core is placed before the open part of the pocket is sealed to enclose the molten core. After the core has been sealed between the sheets, the material may be cut either through the sealed region or around the sealed region to give the individual dosage forms which are then packed either in containers or blister packs. One example of a suitable apparatus for preparing the formulations of the present invention is described in WO-A-9735537.

The invention will now be illustrated by reference to the following examples given by way of example only.

EXAMPLE 1

A film of hydroxypropylmethylcellulose was placed over a vacuum-forming mould in which indentations of the shape of the finished dosage forms were present. The film was heated and vacuum formed to give a film with a plurality of blisters depending from a planar upper surface. Each blister is filled with the appropriate amount of core material prepared as described in Examples 2 to 48 below and a flat film of the same hydroxypropylmethylcellulose attached to the planar upper surface of the vacuum-formed film by applying an adhesive to both the flat film and the planar upper surface and applying pressure to ensure a good seal. The individual capsules are then separated and packed.

EXAMPLE 2

A filled capsule was prepared as follows:

|  | Mg |
|---|---|
| Capsule core: | |
| Hydrogenated coconut oil[1] | 1250 |
| Sucrose[2] | 1275 |
| Flavouring agents[3] | 25 |
| Capsule shell: | |
| Methocel K100 | 6.2 |
| Methocel E50 | 55.8 |
| Glycerine | 10.1 |
| Propylene glycol | 4.8 |
| Citric acid | 3.2 |

[1]RM1216
[2]Celebration Sucrose NCP
[3]Cream Flavour 514388E, Blackcurrant flavour 17.80.3606, natural menthol flavouring.

The capsule of Example 2 is a placebo capsule (i.e. it contains no active agent). It is prepared using a foamed capsule film prepared by pumping nitrogen gas into a concentrated solution of the film composition prior to casting the film composition into a film. The foamed capsule film has a thickness of approximately 150 μm.

The core is prepared by melting the hydrogenated coconut oil at 60-80° C. The flavourings (if present) are then added with stirring until a homogenous mixture is obtained. The sucrose is then added batchwise with mixing to ensure even dispersion.

The appropriate amount(s) of the active agent(s) is/are then dispersed in the product. The resulting capsule core is a solid or semi-solid fondant which must be heated to 50-60° C. before being filled into the blisters of Example 1

EXAMPLE 3-7

The following cores were produced for encapsulation by the capsule film

| Core component | EX3 Mg | EX4 Mg | EX5 Mg | EX6 Mg | EX7 Mg |
|---|---|---|---|---|---|
| Hydrogenated coconut Oil | 1246 | 1250 | 1500 | 1250 | 1139 |
| Sucrose | 1246 | 1250 | 812.5 | 866.7 | 1139 |
| Flubiprofen | 8.75 | — | — | — | — |
| 4-Hexylresorcin | — | 2.4 | — | — | — |
| Dextromethorphan Adsorbate (10% drug) | — | — | 150 | — | — |
| Flavouring | — | — | 37.5 | 50 | — |
| Taste Masked Guaiphenesin (60% drug) | — | — | — | 333.3 | — |
| Taste Masked Ibuprofen (90% drug) | — | — | — | — | 222 |

The flavouring in Example 5 is raspberry flavouring and in Example 6 it is cherry flavouring.

The fondant cores were prepared in accordance with the method detailed in Example 2. The resultant cores were filled into blisters of an unfoamed capsule film material having the following formulation:

|  | % |
|---|---|
| HPMC (Methocel E50 ex Dow) | 75 |
| Anhydrous citric acid | 15 |
| Glycerin | 10 |
| Colourant | q.s. |

The capsule film was about 80 µm thick.

The fondant core of Examples 3 and 4 may be used in capsules intended for the treatment of sore throats; the fondant core of Example 5 may be used in capsules for the treatment of dry coughs; the fondant core of Example 6 may be used in capsules for the treatment of chesty coughs; and the fondant core of Example 7 may be used in capsules for the treatment of headaches and other similar pains or aches.

EXAMPLES 8-12

The following cores were produced for encapsulation by the capsule film

| Core component | EX8 Mg | EX9 Mg | EX10 Mg | EX11 Mg | EX12 Mg |
|---|---|---|---|---|---|
| Hydrognated coconut oil | 1005 | 1000 | 1250 | 1250 | 1100 |
| Sucrose | 1005 | 1000 | 1250 | 1250 | 1100 |
| Aluminium hydroxide | 420 | 500 | — | — | — |

-continued

| Core component | EX8 Mg | EX9 Mg | EX10 Mg | EX11 Mg | EX12 Mg |
|---|---|---|---|---|---|
| Magnesium oxide | 70 | — | — | — | — |
| Senna | — | — | 7.5 | — | — |
| Bisacodyl | — | — | — | 5 | — |
| Pseudoephedrine Hydrochloride | — | — | — | — | 300 |

The fondant cores were prepared in accordance with the method detailed in Example 2. The resultant cores were filled into blisters of an unfoamed capsule film material having the following formulation:

|  | % |
|---|---|
| HPMC (Methocel E50 ex Dow) | 80 |
| Anhydrous citric acid | 5 |
| Propylene glycol | 7.5 |
| Glycerin | 7.5 |
| Colourant | q.s. |

The capsule film had a thickness of about 75 µm.

The fondant core of Examples 8 and 9 may be used in capsules intended for the treatment of indigestion; the fondant core of Examples 10 and 11 may be used in capsules for the treatment of constipation; and the fondant core of Example 12 may be used in capsules for treating cold and flu symptoms.

EXAMPLES 13 AND 14

Capsule cores containing two active agents were prepared as follows:

| Core component | EX13 Mg | EX14 Mg |
|---|---|---|
| Hydrogenated coconut oil | 1139 | 987.5 |
| Sucrose | 1079 | 987.5 |
| Taste Masked Ibuprofen (90% drug content) | 222 | — |
| Pseudoephedrine HCl | 60 | — |
| Paracetamol | — | 500 |
| Diphenylhydramine HCl | — | 25 |

Examples 13 and 14 were prepared in accordance with the method detailed in Example 2. The cores were filled into blisters of an unfoamed capsule film material having the formulation given in Examples 8-12. The filled capsules may be used in the treatment of cold and flu symptoms.

EXAMPLES 15-16

Capsule cores using an alternative low melting point solid organic component were prepared as follows:

| Core component | EX15 Mg | EX16 Mg |
|---|---|---|
| PEG 1000 | 1250 | 1500 |
| Sucrose | 866.7 | 812.5 |
| Flavouring | 50 | 37.5 |

-continued

| Core component | EX15 Mg | EX16 Mg |
|---|---|---|
| Taste Masked Guaiphenesin (60% drug content) | 333.3 | — |
| Dextromethorphan Adsorbate (10% drug content) | — | 150 |

In Example 15, the flavouring was cherry flavouring and in Example 16, it was raspberry flavouring.

Examples 15 and 16 were prepared in accordance with the method detailed in Example 2. The cores were filled into blisters of an unfoamed capsule film material having the formulation given in Examples 8-12. The core of Example 15 may be used in capsules intended for the treatment of chesty coughs and the core of Example 16 may be used in capsules intended for the treatment of dry coughs.

EXAMPLES 17-32

The Examples 1-16 were repeated, except that the sucrose component of the fondant core was replaced with glucose having a mean particle size of 10-15 μm.

EXAMPLES 33-48

The Examples 1-16 were repeated, except that the sucrose component of the fondant core was replaced with fructose having a mean particle size of 15-20 μm.

What is claimed is:

1. A medicinal composition in the form of a capsule comprising
   a) a fondant core comprising a medicinally effective unit dose of one or more active medicaments; and
   b) said medicaments being enclosed within a film material which comprises at least 40% by weight hydroxypropylmethyl cellulose,
   wherein the fondant core comprises a solid organic carrier.

2. A medicinal composition according to claim 1, wherein the solid organic carrier has a melting point in the range 22 to 60° C.

3. A medicinal composition according to claim 1, wherein the solid organic carrier has a melting point in the range 25 to 40° C.

4. A medicinal composition according to claim 1, wherein the core comprises a sugar or sugar derivative having a weight average particle size in the range 1 to 150 μm.

5. A medicinal composition according to claim 4, wherein the core comprises a sugar or sugar derivative having a weight average particle size in the range 10 to 100 μm.

6. A medicinal composition according to claim 5, wherein the core comprises a sugar or sugar derivative having a weight average particle size in the range 10 to 25 μm.

7. A medicinal composition according to claim 1, wherein the core has a viscosity of at least 100 Pa.s when measured at 36° C. at a sheer stress of 1 Pa.

8. A medicinal composition according to claim 1 in which the film material is composed of 40-80% hydroxypropylmethyl cellulose with 20-60% of one or more plasticisers.

9. A medicinal composition according to claim 8, in which the plasticiser is selected from polyethyleneglycols, diacetin, propyleneglycols and glycerin.

10. A medicinal composition according to claim 1, wherein the film material is non-expanded.

11. A medicinal composition according to claim 1, wherein the film material is expanded by pumping a gas into a concentrated solution of the polymer and drying the resulting mixture.

12. A medicinal composition according to claim 1 wherein the active medicament comprises an analgesic, an antacid, a decongestant, a cough suppressant, an expectorant, a mucolytic agent or a laxative.

* * * * *